US010969378B2

(12) United States Patent
Chae et al.

(10) Patent No.: US 10,969,378 B2
(45) Date of Patent: Apr. 6, 2021

(54) STRIP EJECTION APPARATUS FOR BLOOD GLUCOSE METER

(71) Applicant: I-SENS, INC., Seoul (KR)

(72) Inventors: Kyungchul Chae, Gyeonggi-do (KR); Hyunho Choi, Seoul (KR); Goangyel Ryu, Gyeonggi-do (KR); Geunsig Cha, Seoul (KR); Hakhyun Nam, Seoul (KR)

(73) Assignee: I-SENS, INC., Seoul (KR)

( * ) Notice: Subject to any disclaimer, the term of this patent is extended or adjusted under 35 U.S.C. 154(b) by 233 days.

(21) Appl. No.: 16/074,427

(22) PCT Filed: Dec. 30, 2016

(86) PCT No.: PCT/KR2016/015588
§ 371 (c)(1),
(2) Date: Jul. 31, 2018

(87) PCT Pub. No.: WO2017/135579
PCT Pub. Date: Aug. 10, 2017

(65) Prior Publication Data
US 2019/0033285 A1 Jan. 31, 2019

(51) Int. Cl.
*G01N 33/487* (2006.01)
*A61B 5/157* (2006.01)
(Continued)

(52) U.S. Cl.
CPC ..... *G01N 33/4875* (2013.01); *A61B 5/14532* (2013.01); *A61B 5/157* (2013.01); *G01N 33/49* (2013.01)

(58) Field of Classification Search
CPC .... G01N 33/4875; G01N 33/49; A61B 5/157; A61B 5/14532
See application file for complete search history.

(56) References Cited

U.S. PATENT DOCUMENTS 6,506,168 B1   1/2003   Fathallah et al.
6,616,819 B1 * 9/2003   Liamos .............. G01N 27/3272
                                                204/403.02
(Continued)

FOREIGN PATENT DOCUMENTS

CN   101501482   8/2009
CN   201382916   1/2010
(Continued)

OTHER PUBLICATIONS

International Search Report for PCT/KR2016/015588 dated Mar. 29, 2017 and its English translation from WIPO.
(Continued)

*Primary Examiner* — Dennis White
(74) *Attorney, Agent, or Firm* — Ladas & Parry, LLP

(57) ABSTRACT

The present invention relates to a strip ejection apparatus for a blood glucose meter, wherein: an ejector block moving to eject a measurement strip is received in the space inside a housing, whereby it is possible to make the apparatus compact, thereby enhancing space efficiency of the blood glucose meter; components can be mounted on a PCB of the blood glucose meter in units of modules as they are, without any additional separate assembly for the components, whereby it is possible to enhance efficiency of a manufacturing process; a guide protrusion coupled with an ejection switch of the blood glucose meter is selectively formed on the upper or lower portion of the ejector block or formed on both the upper and lower portions thereof, whereby it is possible to enhance the degree of freedom in design of the mounting position of the ejection switch; and the strip ejection apparatus can be applied to various types of blood glucose meters so that it is possible to standardize the type of strip ejection apparatus, thereby reducing manufacturing cost, as well as facilitating component management.

10 Claims, 5 Drawing Sheets

(51) Int. Cl.
*A61B 5/145* (2006.01)
*G01N 33/49* (2006.01)

(56) References Cited

U.S. PATENT DOCUMENTS

| | | |
|---|---|---|
| 2009/0029479 A1 | 1/2009 | Docherty et al. |
| 2009/0108013 A1* | 4/2009 | Van Der Velde ............... G01N 33/4875 221/1 |
| 2010/0012530 A1 | 1/2010 | Watanabe et al. |
| 2010/0276286 A1 | 11/2010 | Nishimura et al. |

FOREIGN PATENT DOCUMENTS

| | | |
|---|---|---|
| CN | 201642023 | 11/2010 |
| CN | 102135523 | 7/2011 |
| CN | 103698528 | 4/2014 |
| EP | 1762848 | 3/2007 |
| JP | 2003-534088 | 11/2003 |
| JP | 2009-31286 | 2/2009 |
| JP | 2009-210278 | 9/2009 |
| KR | 10-1182730 | 9/2012 |
| KR | 10-2013-0075776 | 7/2013 |
| KR | 10-2014-0094931 | 7/2014 |
| WO | 2008/016137 | 2/2008 |
| WO | 2012/037486 | 3/2012 |

OTHER PUBLICATIONS

Written Opinion of the International Searching Authority for PCT/KR2016/015588 dated Mar. 29, 2017 and its English machine translation by Google Translate.

International Preliminary Report on Patentability (Chapter I) for PCT/KR2016/015588 dated Aug. 7, 2018 and its English translation from WIPO Office Action dated May 27, 2020 for Chinese Patent Application No. 201680080370.8 and its English translation provided by Applicant's foreign counsel.

Extended European Search Report dated Mar. 8, 2019 for European Patent Application No. 16889555.5.

Office Action dated Sep. 10, 2019 for Japanese Patent Application No. 2018-540145 and its English machine translation by Google Translate.

Office action from Chinese Patent Application No. 201680080370.8 dated May 27, 2020 with search report, and its English translation provided from the foreign associate.

* cited by examiner

[FIG. 1]
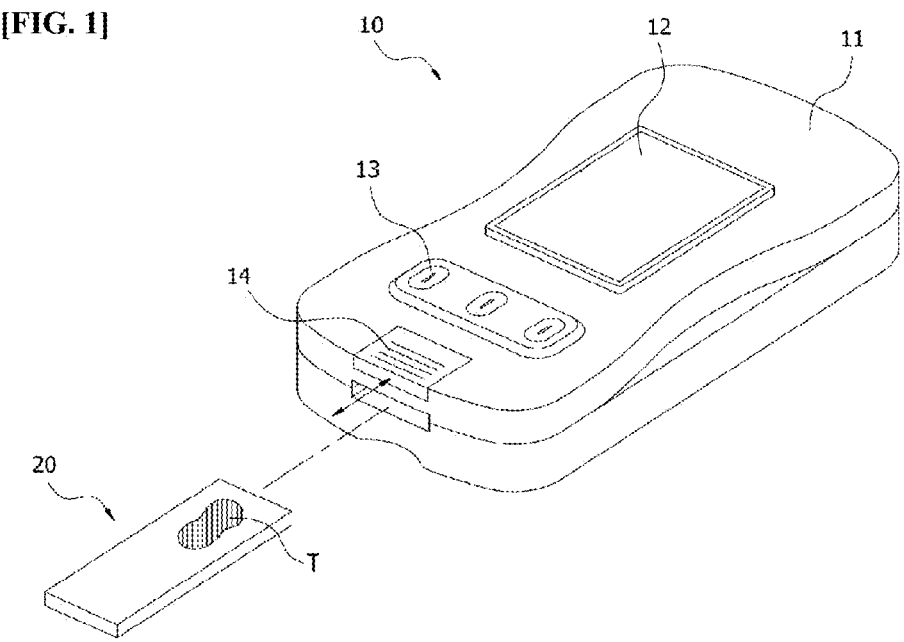
[FIG. 2]
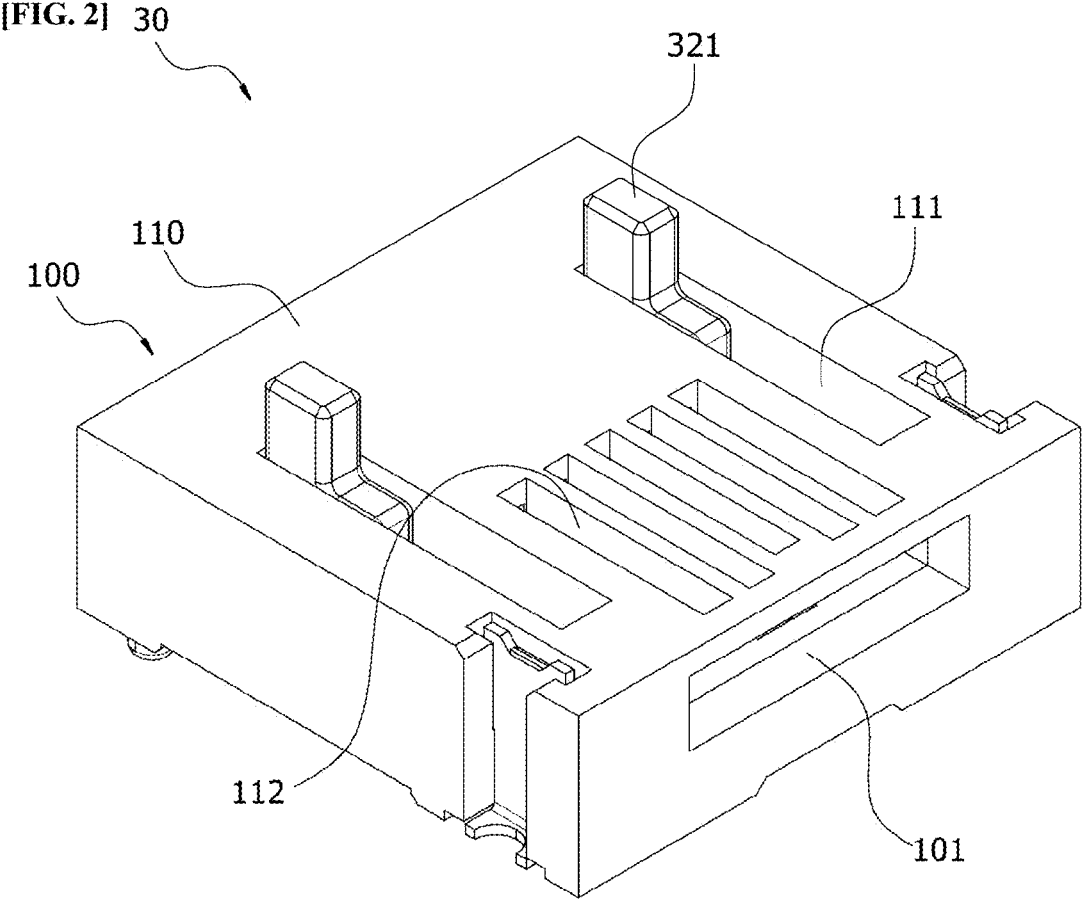

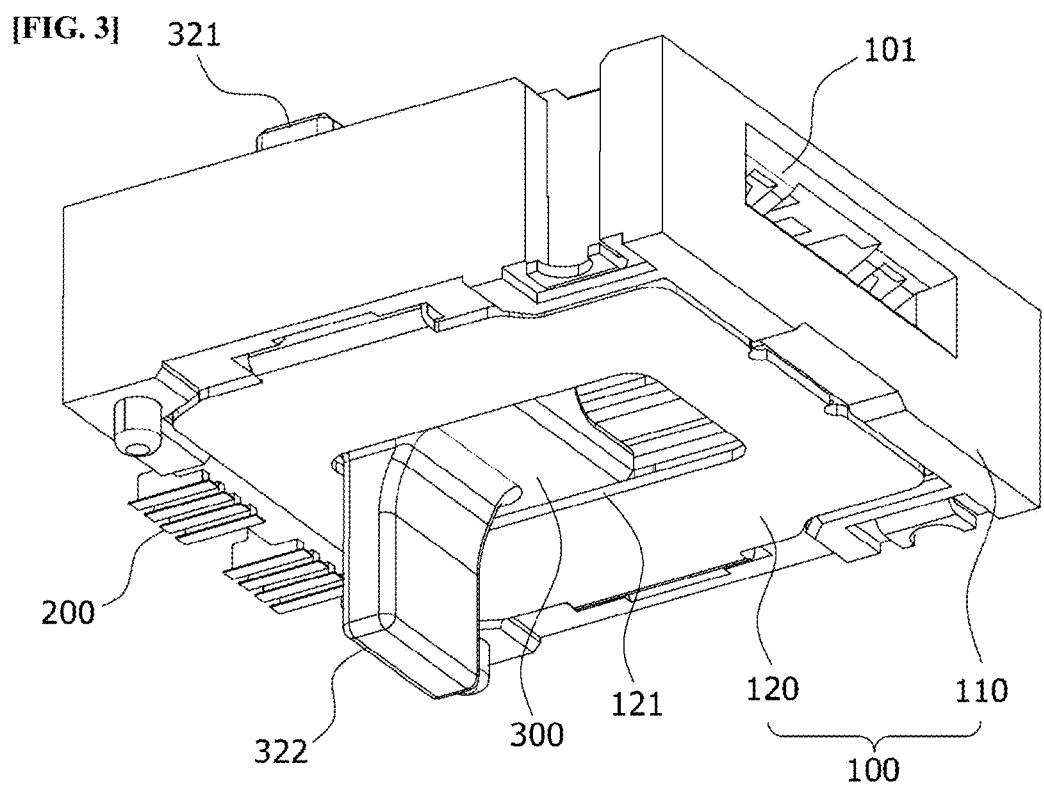

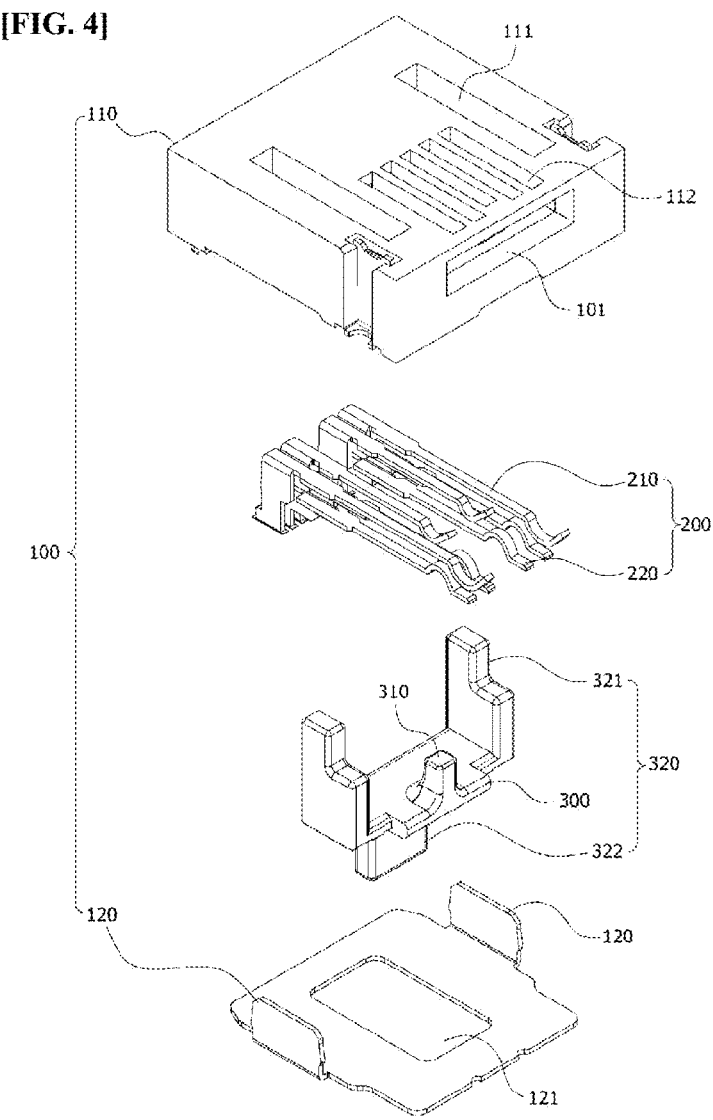

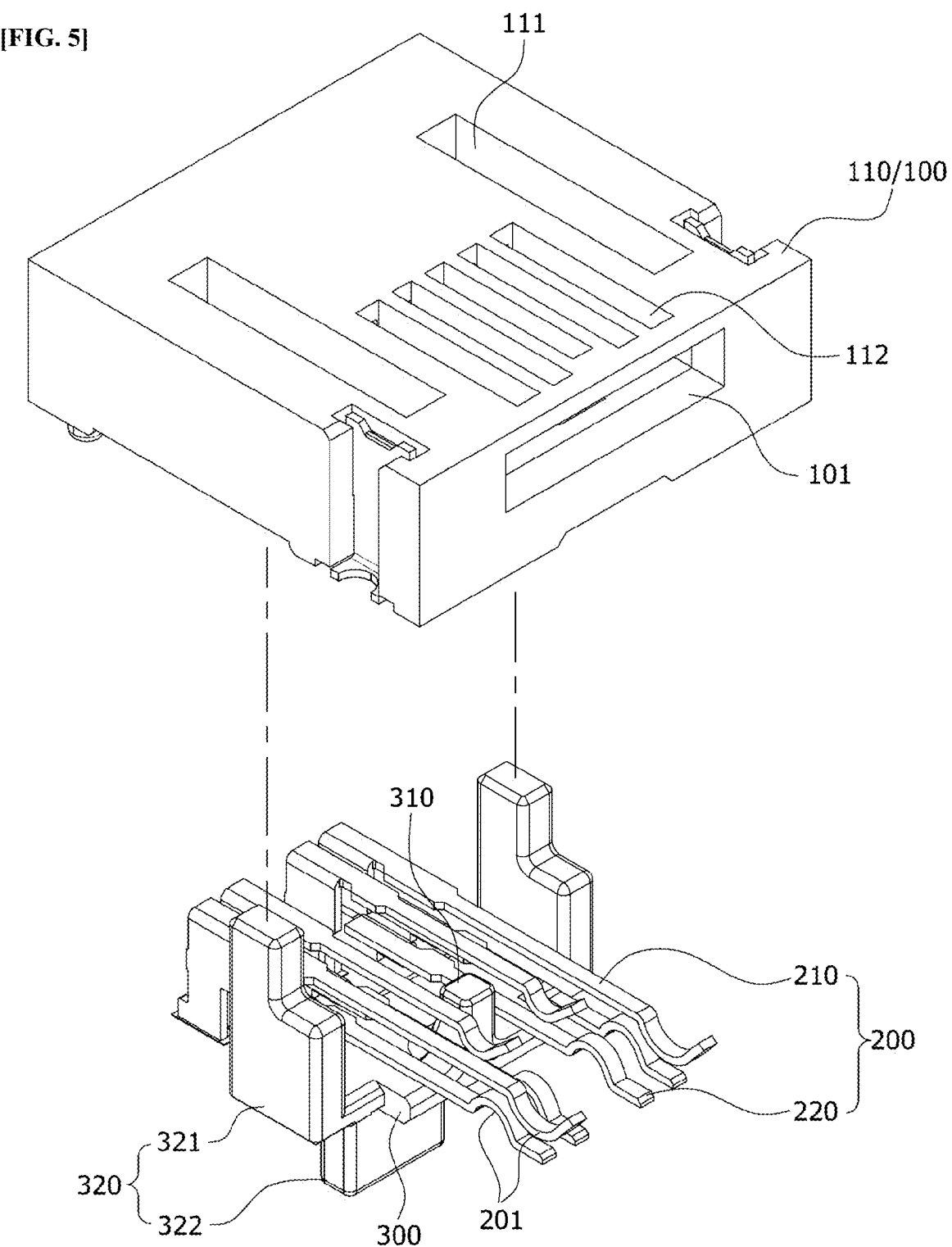
[FIG. 5]

[FIG. 6]
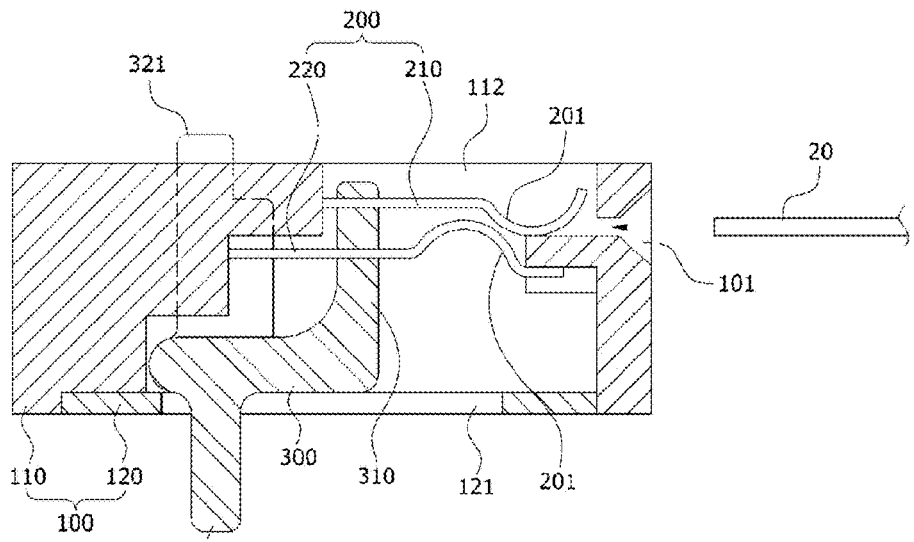
[FIG. 7]
(a)
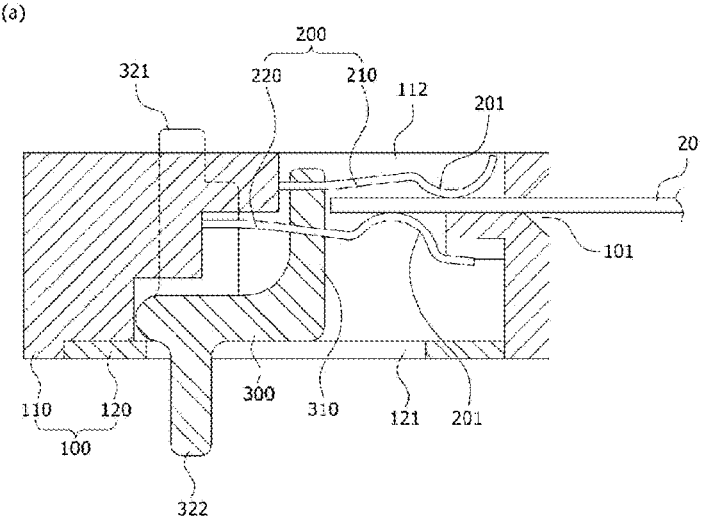
(b)
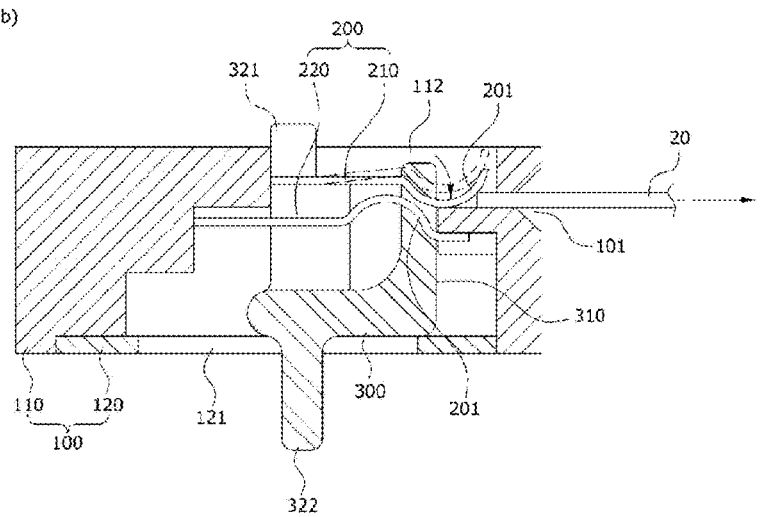

STRIP EJECTION APPARATUS FOR BLOOD GLUCOSE METER

CROSS-REFERENCE TO RELATED APPLICATIONS

This application is the U.S. National Stage of International Patent Application No. PCT/KR2016/015588 filed on Dec. 30, 2016, which claims the priority to Korean Patent Application No. 10-2016-0012525 filed in the Korean Intellectual Property Office on Feb. 1, 2016, the entire contents of which are incorporated herein by reference.

TECHNICAL FIELD

The present disclosure relates to a strip ejection apparatus for a blood glucose meter. More particularly, the present disclosure relates to a strip ejection apparatus for a blood glucose meter, in which an ejector block moving to eject a measurement strip is received in a space inside a housing, whereby it is possible to make the apparatus compact, thereby enhancing space efficiency of the blood glucose meter. Components can be disposed on a printed circuit board (PCB) of the blood glucose meter in units of modules as they are, without any additional separate assembly for the components, whereby it is possible to enhance efficiency of a manufacturing process. A guide protrusion coupled to an ejection switch of the blood glucose meter is selectively formed on the upper or lower portion of the ejector block or is formed on both the upper and lower portions thereof, whereby it is possible to enhance the degree of freedom in design of the mounting position of the ejection switch. The strip ejection apparatus can be applied to various types of blood glucose meters so that it is possible to standardize the type of strip ejection apparatus, thereby reducing manufacturing costs, as well as facilitating component management.

BACKGROUND ART

Diabetes or diabetes mellitus is a chronic medical condition that is common in modern people. In the Republic of Korea, it affects 2 million people, about 5% of the total population.

Diabetes is caused from the absolute deficiency or relative insufficiency of insulin produced by the pancreas, due to various causes such as obesity, stress, poor eating habits, inherited hereditary factors, and thus the sugar in the blood cannot be balanced, but may be absolutely increased.

The blood usually contains a certain concentration of glucose and tissue cells gain energy therefrom.

However, when glucose is increased excessively, it is not properly stored in the liver, muscle, or adipose tissue and accumulates in the blood. As a result, patients with diabetes maintain a much higher blood sugar level than other people. Excessive blood sugar passes through the tissues and is discharged into the urine, resulting in deficiency of sugar, which is absolutely necessary for each tissue of the body, thereby causing abnormalities in respective tissues of the body.

Diabetes mellitus is characterized by the absence of subjective symptoms at the beginning. When diabetes progresses, diabetes-specific symptoms such as diarrhea, polyuria, weight loss, general anxiety, skin itchiness, and scarring of the hands and feet are present. Further progression of diabetes leads to complications such as visual disturbances, hypertension, kidney disease, paralysis, periodontal disease, muscle spasms and neuralgia, and gangrene.

Systematic blood glucose measurement and treatment should be performed to diagnose such diabetes beforehand and manage the condition so as not to progress to diabetes and its complications.

For people with diabetes or those who have not yet developed diabetes, but have higher blood sugar than normal, medical device manufacturers offer a variety of blood glucose meters to measure blood glucose at home.

FIG. 1 is a schematic view illustrating the configuration of a conventional blood glucose meter.

As illustrated in FIG. 1, the blood glucose meter 10 is configured such that a test strip 20 is loaded into a casing 11, a blood sample T of a subject is dropped and absorbed by the loaded test strip 20, the blood sample T absorbed by the test strip is measured for the blood glucose level by a blood sugar measuring module provided in the casing 11, and the measured result for the blood sugar level is displayed on a display 12. Functional switches 13 are provided to the casing 11 in order for a user to manipulate and operate the blood glucose meter.

After measuring blood sugar levels, repeatedly, the used test strip 20 is removed from the blood glucose meter 10 and a new test strip 20 is loaded into the casing for a subsequent test.

Here, when a user directly holds and removes the test strip 20 in the process of removal of the test strip 20 from the blood glucose meter 10, a tester or a subject may come into contact with the blood sample remaining in the test strip 20 on his/her hand. Thus, when a new test strip 20 is loaded into the blood glucose meter, the blood sample on his/her hand may contaminate the new test strip, resulting in misdiagnosis of the blood sugar level. To prevent this problem, the tester or the subject disadvantageously needs to wash his/her hands or to change his/her sanitary gloves whenever he/she tries to make a test.

Thus, to solve these problems, the casing 11 of the blood glucose meter 10 is generally provided with a strip unloader 14 to unload the loaded test strip 20 from the casing 11. The strip unloader 14 is slidably disposed on one side of the casing 11, so that, when a user pulls out the strip unloader 14, it can be slid out of the casing 11, together with the test strip 20.

Here, a strip unloading device (not shown) is disposed inside of the casing 11 to unload the test strip 20 according to the manipulation of the strip unloader 14. A conventional strip unloading device, however, has problems of complicated structure and assembly, which increases manufacturing costs or the size of the blood glucose meter itself. Also, the conventional strip unloading device has another problem in that it needs to have a dedicated structure for a specific blood glucose meter, so it requires different designs for various types of blood glucose meters, which greatly limits the degree of freedom in design for both a blood glucose meter and a strip unloader.

DISCLOSURE

Technical Problem

Accordingly, the present disclosure has been made in consideration of the above-described problems occurring in the related art, and the present disclosure proposes a strip unloading device for a blood glucose meter, wherein an unloader block, movable for unloading a test strip, is accommodated in a housing such that the unloader block is disposed on a PCB of the blood glucose meter in a module type as it is, without separate additional assembly, thereby minimizing the size thereof and thus improving space efficiency of the blood glucose meter, and improving manufacturing efficiency.

Another object of the present disclosure is to provide a strip unloading device for a blood glucose meter, wherein a guide protrusion coupled to a strip unloader of the blood glucose meter is selectively formed on the upper or lower portion of an unloader block or formed on both the upper and lower portions thereof, whereby it is possible to enhance the degree of freedom in design of the mounting position of the strip unloader and the strip unloading device can be applied to various types of blood glucose meters so that it is possible to standardize the type of strip unloading device, thereby reducing manufacturing costs, as well as facilitating component management.

A further object of the present disclosure is to provide a strip unloading device for a blood glucose meter, wherein a test strip is elastically supported by contact pins in the space of the housing, thereby enhancing the fixed loading of the loaded test strip and complete unloading of the unloaded test strip by means of elastic force of the contact pins and thus ensuring user convenience in use.

Technical Solution

According to an aspect of the present disclosure, a strip unloading device for a blood glucose meter is provided, the strip unloading device being disposed in the blood glucose meter to unload a test strip loaded therein, the strip unloading device including: a housing having a storage space therein and having on one side thereof a strip insert into which the test strip is inserted; a plurality of contact pins disposed in the housing to contact upper and lower surfaces of the test strip loaded into the strip insert; and an unloader block disposed in the housing below the contact pins to linearly move towards or away from the strip insert and having a central unloading protrusion to be engaged with the test strip loaded into the strip insert so as to eject the test strip in the process of moving towards the strip insert, wherein the contact pins are disposed on opposite sides of the unloader block in a width direction thereof relative to the unloading protrusion.

Here, a guide protrusion may be provided on at least one of upper and lower surfaces of the unloader block to extend out through the housing so as to be engaged with a strip unloader disposed on the blood glucose meter, and the housing may have a guide hole to guide a movement path of the guide protrusion moving along with the unloader block.

In addition, the housing may have an upper housing part with a lower side opened, and a lower housing part coupled to the lower side of the upper housing part, wherein the unloader block is seated on and slidably moves along an upper surface of the lower housing part.

Furthermore, guide protrusions may be respectively provided on opposite sides of the upper surface of the unloader block, and a guide protrusion may be provided at the center of the lower surface of the unloader block, wherein the contact pins are disposed between the opposite sides of the upper surface of the unloader block.

In addition, the contact pins may consist of a plurality of upper contact pins and a plurality of lower contact pins, which are vertically separated from each other to contact the upper and lower surfaces of the test strip, respectively, wherein one-side ends of the upper and lower contact pins are configured to elastically compress the upper and lower surfaces of the test strip loaded into the strip insert, respectively.

Furthermore, the housing may be provided with a plurality of guide holes to guide an elastic deformation path of the contact pins.

In addition, one-end sides of the upper and lower contact pins may be respectively provided with elastic contact parts curved downwardly or upwardly to elastically contact the upper and lower surfaces of the test strip.

Furthermore, the elastic contact parts of the upper and lower contact pins may be sequentially formed in different positions along the movement direction of the unloader block.

Advantageous Effects

As set forth above, the unloader block movable for unloading a test strip is accommodated in a housing such that the unloader block is disposed on a PCB of the blood glucose meter in a module type as it is, without separate additional assembly, thereby minimizing the size thereof and thus improving space efficiency of the blood glucose meter, and improving manufacturing efficiency.

In addition, the guide protrusion coupled to a strip unloader of the blood glucose meter is selectively formed on the upper or lower portion of an unloader block or formed on both the upper and lower portions thereof, whereby it is possible to enhance the degree of freedom in design of the mounting position of the strip unloader and the strip unloading device can be applied to various types of blood glucose meters so that it is possible to standardize the type of strip unloading device, thereby reducing manufacturing costs, as well as facilitating component management.

Furthermore, the test strip is elastically supported by the contact pins in the space of the housing, thereby enhancing the fixed loading of the loaded test strip and complete unloading of the unloaded test strip by means of elastic force of the contact pins and thus ensuring user convenience in use.

DESCRIPTION OF DRAWINGS

FIG. 1 is a schematic view illustrating the configuration of a conventional blood glucose meter;

FIG. 2 is a front perspective view schematically illustrating an appearance of a strip unloading device for a blood glucose meter according to an embodiment of the present disclosure;

FIG. 3 is a bottom perspective view schematically illustrating an appearance of a strip unloading device for a blood glucose meter according to an embodiment of the present disclosure;

FIG. 4 is an exploded perspective view schematically illustrating the configuration of a strip unloading device for a blood glucose meter according to an embodiment of the present disclosure;

FIG. 5 is a partially exploded perspective view schematically illustrating the mutual arrangement between contact pins and an unloader block in the strip unloading device for a blood glucose meter according to an embodiment of the present disclosure;

FIG. 6 is a cross-sectional view schematically illustrating an internal configuration of the strip unloading device for a blood glucose meter according to an embodiment of the present disclosure; and FIG. 7 is a view schematically illustrating the operation of the strip unloading device for a blood glucose meter according to an embodiment of the present disclosure.

BEST MODE

Reference will now be made in greater detail to a preferred embodiment of the invention, an example of which is illustrated in the accompanying drawings. Wherever possible, the same reference numerals will be used throughout the drawings and the description to refer to the same or like parts. In the following description, it is to be noted that, when the functions of conventional elements and the detailed description of elements related to the present disclosure may render the gist of the present invention unclear, a detailed description of those elements will be omitted.

FIGS. 2 and 3 are respectively front and bottom perspective views schematically illustrating an appearance of a strip unloading device for a blood glucose meter according to an embodiment of the present disclosure, FIG. 4 is an exploded perspective view schematically illustrating the configuration of the strip unloading device for a blood glucose meter according to an embodiment of the present disclosure, FIG. 5 is a partially exploded perspective view schematically illustrating the mutual arrangement between contact pins and an unloader block in the strip unloading device for a blood glucose meter according to an embodiment of the present disclosure, FIG. 6 is a cross-sectional view schematically illustrating an internal configuration of the strip unloading device for a blood glucose meter according to an embodiment of the present disclosure, and FIG. 7 is a view schematically illustrating the operation of the strip unloading device for a blood glucose meter according to an embodiment of the present disclosure.

The strip unloading device for a blood glucose meter is a device that is installed inside of the blood glucose meter to unload a test strip loaded into the blood glucose meter, and includes a housing 100, a plurality of contact pins 200, and an unloader block 300.

The housing 100 is formed like a vessel having a storage space therein, and may have a shape such as a rectangle or other shapes as shown in FIGS. 2 and 3. The housing 100 has a strip insert 101 on one side thereof, into which a test strip 20 is inserted and loaded.

As illustrated in FIG. 4, the housing 100 may include an upper housing part 110 having a vessel shape with a lower side opened, and a lower housing part 120 coupled to the lower side of the upper housing part 110. The unloader block 300 which can move linearly in the housing 100 may be slidably seated on an upper surface of the lower housing part 120. Here, the upper housing part 110 may be formed of synthetic resin, e.g. liquid crystal polymer (LCP), and the lower housing part 120 may be formed of a metallic material, e.g. stainless steel, for easy sliding motion of the unloader block 300.

The contact pins 200 serve to contact an electrode terminal formed on the surface of the test strip 20 loaded into the strip insert 101 so as to transmit an electric signal generated from the test strip 20 to a glucose measuring module of the bold glucose meter. The contact pins are configured to be disposed in the housing so as to contact upper and lower surfaces of the test strip 20 inserted and loaded into the strip insert 101. The contact pins 200 consist of a plurality of upper contact pin parts 210 and a plurality of lower contact pin parts 220, which are separately disposed to contact the upper and lower surfaces of the test strip 20.

The unloader block 300 is disposed in the housing 100 below the plurality of contact pins 200 so as to linearly reciprocate close to or away from the strip insert 101. The unloader block has an unloading protrusion at the center of the upper surface to engage with the test strip inserted into the strip insert 101 and unload the test strip out of the strip insert while moving close to the strip insert 101. The unloader block 300 may be formed of liquid crystal polymer for the improvement of assembly of a blood glucose meter.

Here, as illustrated in FIG. 5, the contact pins 200 are disposed on opposite sides of the unloader block in a direction perpendicular to a movement direction of the unloader block 300 relative to the unloading protrusion 310, i.e. on opposite sides in a width direction of the unloader block 300.

The unloader block 300 is configured to move linearly in association with the strip unloader 14 (see FIG. 1) slidably disposed on a blood glucose meter. To this end, the unloader block 300 is provided with a guide protrusion 320, which extends out through the housing 100 so as to be coupled to the strip unloader 14. Although not shown, the strip unloader 14 may be provided on an inner surface thereof with a coupling part (not shown) into which the guide protrusion 320 is interference-fitted.

The guide protrusion 320 may be formed on at least one of the upper and lower surfaces of the unloader block 300. That is, the guide protrusion 320 may be formed on the upper surface, the lower surface, or both the upper and lower surfaces of the unloader block 300, if needed.

FIGS. 2 to 5 show the embodiment in which the guide protrusions 320 are formed on both the upper and lower surfaces of the unloader block 300. The guide protrusions 321 formed on the upper surface of the unloader block 300 may be disposed on opposite sides of the unloader block 300 in the width direction thereof, and the guide protrusion 322 formed on the lower surface of the unloader block 300 may be disposed at the center of the unloader block 300.

Correspondingly, the housing 100 is provided with guide holes 111, 121 to guide a movement path of the guide protrusions 320 and the unloader block 300 having the same so as to move along with the guide protrusions. That is, the upper housing part 110 has the guide holes 111 through which the guide protrusions 321 formed on the upper surface of the unloader block 300 is inserted and guided therealong, and the lower housing part 120 has the guide hole 121 through which the guide protrusion 322 formed on the lower surface of the unloader block 300 is inserted and guided therealong.

In this case, the upper contact pins 210 are disposed between the guide protrusions 321 formed on opposite sides of the upper surface of the unloader block 300.

According to the configuration of the present disclosure, since the strip unloading device is completely assembled with the unloader block 300 disposed in the housing 100, and the strip unloading device is assembled with a blood glucose meter in a single module type, the size of the entire device can be miniaturized, and the assembly can be quickly and easily performed. In addition, since the guide protrusions 320 are formed to protrude out of the housing 100, a mounting position of the strip unloader 14 of a blood glucose meter can be freely selected according to a user's need.

More specifically, the strip unloading device is configured such that the contact pins 200 are disposed on opposite sides of the unloading protrusion 310 of the unloader block 300, securing the movement path of the unloading protrusion 310 so that the unloader block 300 can be accommodated in the housing 100, and the entire size of the strip unloading device can be miniaturized.

In addition, in the assembly of a blood glucose meter, the strip unloading device is disposed on the blood glucose meter such that contact pins 200 are soldered to a PCB (not shown) in the blood glucose meter. Here, since the unloader block 300 is accommodated in the housing 100, the entire strip unloading device can be disposed as a module to the PCB as it is, without an additional process of assembling the unloader block 300, or the like. Furthermore, since the soldering is performed in a high temperature process, the unloader block 300 is preferably formed of heat-resistant liquid crystal polymer (LCP) to prevent the unloader block 300 from being damaged in the high temperature process.

In addition, since the guide protrusions 320 to be coupled to the strip unloader 14 of the blood glucose meter are disposed to protrude upwardly and downwardly from the housing 100, in the process of designing mounting positions of the strip unloader 14 in association with various types of blood glucose meters, the mounting positions can be freely selected to be the upper or lower surface of the blood glucose meter, without a structural change in the strip unloading device, particularly the unloader block 300. That is, the degree of freedom in design of the mounting position of the strip unloader 14 can be improved, so that the strip unloader 14 can be freely applied to the same unloader block 300 and the strip unloading device having the same without replacement of components, thereby facilitating management of components and improving manufacturing efficiency.

Here, as described before, the contact pins 320 consist of upper contact pins 210 and lower contact pins 220, respective one ends of which are configured to elastically compress the upper and lower surfaces of the test strip 20 loaded into the strip insert 101.

That is, as illustrated in FIGS. 5 and 6, the upper and lower contact pins 210 and 220 are formed from an elastic metal plate elongated in one direction, such that one end thereof contact the surface of the test strip 20, and the other end thereof is fixed to the housing 100. According to this structure, the upper and lower contact pins 210 and 220 can elastically compress the opposite surfaces of the test strip 20 in a vertical direction with their own elastic force.

Here, the housing 100 may be provided with guide holes 112 to guide a vertically elastic deformation path of the upper and lower contact pins 210 and 220, while guiding the positions of the upper and lower contact pins 210 and 220. Thus, when the test strip 20 is inserted and loaded into the housing 100 through the strip insert 101, the test strip 20 is elastically fixedly held with the elastic force vertically applied to the opposite surfaces thereof from the upper and lower contact pins 210 and 220.

With the configuration in which the upper and lower elastic contact pins 210 and 220 of the contact pin 200 elastically contact and compress the test strip 20, a basic function of transmitting an electric signal from the test strip 20 to the PCB of a blood glucose meter, as well as a function of holding the position of the test strip 20, which has been loaded into the strip insert 101, is carried out.

Here, elastic contact parts 201 are formed on one-side ends of the upper and lower contact pins 210 and 220 such that they elastically contact the upper and lower surfaces of the test strip 20, respectively. The elastic contact part 201 of the upper contact pin 210 is downwardly curved, and the elastic contact part of the lower contact pin is upwardly curved. This structure increases elastic force applied to the test strip 20 to thereby enhance a function of fixing the position of the test strip 20.

In addition, as illustrated in FIGS. 5 and 6, the elastic contact parts 201 formed on the upper and lower contact pins 210 and 220 may be sequentially located in different positions according to the movement direction of the unloader block 300. According to the shapes and positions of the elastic contact parts 201, the test strip 20 can be clearly unloaded to the outside in the unloading process of the test strip 20.

More specifically, as illustrated in (a) and (b) of FIG. 7, when the unloader block 300 is moved towards the strip insert 101 with the test strip loaded into the strip insert 101 (which movement of the unloader block 300 is performed by sliding the strip unloader 14), the test strip 20 is pushed out towards the outside of the strip insert 101 due to engagement with the unloading protrusion of the unloader block 300. Here, the test strip 20 is pushed out in a state of being elastically compressed by the elastic contact parts 201 of the upper and lower contact pins 210 and 220, such that according to the sequential arrangement of the elastic contact parts 201, when the test strip 20 is pushed out over the closest elastic contact part 201 of the upper contact pin 210 to the strip insert 101, that elastic contact part 201 slightly elastically moves downwardly as shown in (b) of FIG. 7, which strongly pushes out the test strip 20 to the outside with the downward elastic force, thereby strongly ejecting and unloading the test strip 20 to the outside.

That is, the test strip 20 is first moved towards the outside by the movement of the unloader block 300, and when it is moved over the closest elastic contact part 201 of the upper contact pin 210 to the strip insert 101, the test strip is intensively ejected and unloaded to the outside with a downward elastic motion of the closest elastic contact part 201. Since the strong ejecting force is not caused from the unloader block 300, in a subsequent movement path, the movement of the test strip 20 is automatically carried out without the movement of the unloader block 300.

In other words, although the unloader block 300 is not completely moved to an inlet of the strip insert 101, the test strip 20 can be automatically completely ejected to the outside of the housing 100 with the elastic force of the contact pins 320, thereby allowing the test strip to be conveniently ejected and unloaded without direct manual removal of the test strip 20 by a user.

The foregoing descriptions of specific exemplary embodiments of the present disclosure have been presented with respect to the drawings and are not intended to be exhaustive or to limit the present disclosure to the precise forms disclosed, and obviously many modifications and variations are possible for a person having ordinary skill in the art in light of the above teachings. It is intended therefore that the scope of the present disclosure not be limited to the foregoing embodiments, but be defined by the Claims appended hereto and their equivalents.

The invention claimed is:

1. A strip unloading device for a blood glucose meter, disposed in the blood glucose meter to unload a test strip loaded therein, the strip unloading device comprising:
   a housing having a storage space therein and having on one side thereof a strip insert into which the test strip is inserted;
   a plurality of contact pins disposed in the housing to contact upper and lower surfaces of the test strip loaded into the strip insert; and
   an unloader block disposed in the housing below the contact pins to linearly move towards or away from the strip insert and having a central unloading protrusion to be engaged with the test strip loaded into the strip insert so as to eject the test strip in the process of moving towards the strip insert, wherein the contact pins are disposed on opposite sides of the unloader block in a width direction thereof relative to the unloading protrusion, wherein guide protrusions are provided on upper and lower surfaces of the unloader block to extend out through the housing so as to be engaged with a strip unloader disposed on the blood glucose meter, and the housing has a guide hole to guide a movement path of one of the guide protrusions moving along with the unloader block, and wherein at least two the guide protrusions are respectively provided on opposite sides of the upper surface of the unloader block in the width direction, and the one of the guide protrusions is provided at the center of the lower surface of the unloader block with respect to the width direction.

2. The strip unloading device according to claim 1, wherein the housing had an upper housing part with a lower side opened, and a lower housing part coupled to the lower side of the upper housing part, wherein the unloader block is seated on and slidably moves along an upper surface of the lower housing part.

3. The strip unloading device according to claim 2, wherein the contact pins are disposed between the opposite sides of the upper surface of the unloader block.

4. The strip unloading device according to claim 1, wherein the contact pins comprise a plurality of upper contact pins and a plurality of lower contact pins, which are vertically separated from each other to contact the upper and lower surfaces of the test strip, respectively, wherein one-side ends of the upper and lower contact pins are configured to elastically compress the upper and lower surfaces of the test strip loaded into the strip insert, respectively.

5. The strip unloading device according to claim 4, wherein the housing is provided with a plurality of guide holes to guide an elastic deformation path of the contact pins.

6. The strip unloading device according to claim 4, wherein one-end sides of the upper and lower contact pins are respectively provided with elastic contact parts curved downwardly or upwardly to elastically contact the upper and lower surfaces of the test strip.

7. The strip unloading device according to claim 6, wherein the elastic contact parts of the upper and lower contact pins are sequentially formed in different positions along the movement direction of the unloader block.

8. The strip unloading device according to claim 1, wherein the contact pins comprise a plurality of upper contact pins and a plurality of lower contact pins, which are vertically separated from each other to contact the upper and lower surfaces of the test strip, respectively, wherein one-side ends of the upper and lower contact pins are configured to elastically compress the upper and lower surfaces of the test strip loaded into the strip insert, respectively.

9. The strip unloading device according to claim 2, wherein the contact pins comprise a plurality of upper contact pins and a plurality of lower contact pins, which are vertically separated from each other to contact the upper and lower surfaces of the test strip, respectively, wherein one-side ends of the upper and lower contact pins are configured to elastically compress the upper and lower surfaces of the test strip loaded into the strip insert, respectively.

10. The strip unloading device according to claim 3, wherein the contact pins comprise a plurality of upper contact pins and a plurality of lower contact pins, which are vertically separated from each other to contact the upper and lower surfaces of the test strip, respectively, wherein one-side ends of the upper and lower contact pins are configured to elastically compress the upper and lower surfaces of the test strip loaded into the strip insert, respectively.

* * * * *